(12) United States Patent
Mills et al.

(10) Patent No.: US 9,593,364 B2
(45) Date of Patent: Mar. 14, 2017

(54) DETECTING A TARGET MOLECULE IN A SAMPLE USING A DUAL-ANTIBODY QUANTITATIVE FLUORESCENCE-BASED DETECTION METHOD

(71) Applicant: SRC, Inc., North Syracuse, NY (US)

(72) Inventors: Jeffrey H. Mills, Liverpool, NY (US); Huda S. Suliman, North Syracuse, NY (US); Stacey A. Massulik, Syracuse, NY (US); Frances L. Stites, Ashburn, VA (US); Timothy F. Moshier, Fulton, NY (US); Kenton A. Doctor, East Syracuse, NY (US); Lisa H. Chamberlin, East Syracuse, NY (US); Justin P. Andrews, Camillus, NY (US); Stephen R. Houghton, Tully, NY (US)

(73) Assignee: SRC, INC., North Syracuse, NY (US)

( * ) Notice: Subject to any disclaimer, the term of this patent is extended or adjusted under 35 U.S.C. 154(b) by 247 days.

(21) Appl. No.: 14/283,294

(22) Filed: May 21, 2014

(65) Prior Publication Data
US 2014/0349299 A1 Nov. 27, 2014

Related U.S. Application Data

(60) Provisional application No. 61/825,615, filed on May 21, 2013.

(51) Int. Cl.
*C12P 19/34* (2006.01)
*C12Q 1/68* (2006.01)
(52) U.S. Cl.
CPC ....... *C12Q 1/6804* (2013.01); *G01N 2458/10* (2013.01)

(58) Field of Classification Search
USPC .................................. 435/6.12, 91.1, 91.2
See application file for complete search history.

(56) References Cited

U.S. PATENT DOCUMENTS

| | | | |
|---|---|---|---|
| 6,878,515 B1 | 4/2005 | Landegren | |
| 7,914,987 B2 * | 3/2011 | Fredriksson | C12Q 1/6804 |
| | | | 435/6.1 |

(Continued)

FOREIGN PATENT DOCUMENTS

| | | |
|---|---|---|
| WO | 2004094456 | 11/2004 |
| WO | 2007107743 | 9/2007 |

(Continued)

*Primary Examiner* — Kenneth Horlick
(74) *Attorney, Agent, or Firm* — Blaine T. Bettinger; Bond, Schoeneck & King, PLLC

(57) ABSTRACT

A kit and method for detection of a target in a sample. An assay mixture provided in the kit and used in the method includes a first probe with a first antibody recognizing a first epitope of the target and conjugated to an RNA oligonucleotide; a second probe with a second antibody recognizing a second epitope of the target and conjugated to a DNA oligonucleotide; a reverse primer with a first region complimentary to the RNA oligonucleotide and a second region complimentary to the DNA oligonucleotide; and a reverse transcriptase that creates a DNA transcription product from the RNA oligonucleotide using the reverse primer only if the RNA oligonucleotide and the DNA oligonucleotide are in close proximity. If the target is present in the sample, the reverse primer binds the RNA oligonucleotide and the DNA oligonucleotide to bring the RNA oligonucleotide and the DNA oligonucleotide in close proximity.

19 Claims, 6 Drawing Sheets

(56) References Cited

U.S. PATENT DOCUMENTS

| | | | |
|---|---|---|---|
| 7,932,060 B2* | 4/2011 | Nadeau | C12Q 1/6851 |
| | | | 435/6.1 |
| 2002/0051986 A1 | 5/2002 | Baez et al. | |
| 2007/0026430 A1* | 2/2007 | Andersen | C12Q 1/6813 |
| | | | 435/6.18 |
| 2008/0131883 A1* | 6/2008 | Adams | C07K 16/3069 |
| | | | 435/6.12 |

FOREIGN PATENT DOCUMENTS

| | | |
|---|---|---|
| WO | 2009021031 | 2/2009 |
| WO | 2012104261 | 8/2012 |

* cited by examiner

DETECTING A TARGET MOLECULE IN A SAMPLE USING A DUAL-ANTIBODY QUANTITATIVE FLUORESCENCE-BASED DETECTION METHOD

CROSS-REFERENCE TO RELATED APPLICATIONS

This application claims priority to U.S. Provisional Patent Application Ser. No. 61/825,615, filed on May 21, 2013, and entitled "Methods And Systems For Quantitative Fluorescence-Based Detection Of Molecules And Proteins," the entire disclosure of which is incorporated herein by reference.

BACKGROUND

1. Field of Invention

The present invention relates to methods and systems for the identification of biological threats, and, more particularly, to a novel fluorescence-based assay for the detection of molecules and proteins.

2. Background of Art

There is a continued need for innovative approaches for the identification of biological threats, including Staphylococcal enterotoxin B (SEB), among many others. SEB is a protein produced by the bacterium *Staphylococcus aureus* that acts as a potent enterotoxin. While SEB is the toxin most commonly associated with food poisoning, it is also classified as a potential biological weapon as it is very stable, easily aerosolized, and causes great harm and incapacitation (including death) upon inhalation. The harmful effects of SEB are due to its ability to induce a massive and nonspecific activation of the immune system causing a toxic shock due to the high concentrations of cytokines released into the body. SEB, considered a superantigen, is toxic because of its ability to bind to and crosslink/activate immune cells. Therefore, SEB toxicity is not due to any inherent enzymatic activity. Specifically, the toxicity of SEB is associated with two defined binding sites located on the surface of the SEB protein itself; one binding site for the T-cell receptor (TCR) and the other for the major histocompatibility complex (MHC) class II.

Existing assays available for SEB detection are based on Enzyme Linked Immunosorbent Assays ("ELISA") technology. Quantitative forms of these ELISA-based detection assays are complex, time consuming and more suited for laboratory analysis. Fieldable versions of the ELISA-based assays, commonly referred to as hand-held assays ("HHA"), are not quantitative and have limited sensitivity. Additionally, all these assays are only capable of detecting the presence of SEB, without giving any indication of toxin activity/toxicity.

Accordingly, there is a continued need for methods and systems that quickly and effectively identify the biological toxin and provide quantitative information about the toxin activity/toxicity.

BRIEF SUMMARY

In accordance with the foregoing objects and advantages, methods and systems are provided for detecting molecules and proteins, such as biological toxins, and providing quantitative information pertaining to molecule/protein concentration and/or toxin activity/toxicity.

According to an embodiment is provided a quantitative one-step "activity" assay that can be performed inside or outside of a laboratory environment, and which can determine the threat level of an exposure or attack, including but not limited to the detection and activity of Staphylococcal enterotoxin B ("SEB"). The assay, which can be called the Proximity Activated PCR Assay ("PAPA"), for example, is a novel and simple-to-use detection assay that can identify and quantify any molecule or protein. This new technology incorporates the detection specificity of antibody binding with an initiation step that requires reverse transcriptase Polymerase Chain Reaction ("PCR") and precise oligonucleotide interactions that are dependent on proximity/distance to activate a quantitative fluorescence-based PCR signal amplification reaction. According to an embodiment, the assay can be quickly run on any fluorescence-based PCR amplification platform in the lab or field.

According to one embodiment, the PAPA overcomes the complexities associated with developing an assay to detect and identify SEB toxin activity. SEB toxicity is a consequential result of binding events that over-excite the immune system, and not associated with a specific product produced. To detect SEB activity, there was a need to utilize a molecular binding-based assay for detection. The crucial cross-linking binding sites on SEB for the TCR and MHC class II molecule have been mapped and therefore the toxic activity of an SEB molecule can be determined by verifying the presence of the TCR and MHC class II binding sites on the SEB molecule. To detect the toxic potential of a single SEB molecule, the PAPA requires dual antibody binding event utilizing available monoclonal antibodies that bind to the epitopes of the TCR and MHC class II binding sites. Any mutation in either of these binding sites, which would prevent dual antibody binding, would also make the SEB molecule non-toxic; as it would be unable to cross-link the TCR and the MHC class II molecule on cells within the immune system. Therefore, utilizing two distinct antibody clones that bind to different sites on the same molecule is an important component of the PAPA design.

While a dual antibody binding event on an SEB molecule can determine its toxicity, it was also necessary to determine a way to associate a successful dual antibody binding event to the generation of measureable signal. One technology that utilizes antibody binding to a molecule in order to generate a signal are ELISAs. Sandwich ELISAs utilize two antibodies to the same molecule; one to capture the molecule to an assay plate and the other to bind to the "captured" molecules in order to detect and quantify the amount of molecule present. This detection typically utilizes enzymes that react with chromogenic reporter substrates to produce a change in color that is used as a signal. While ELISAs produce useful information, they are time consuming (5 to 6 hours), require multiple wash and incubation steps, and are typically designed for lab based experimentation. Therefore, ELISA based technology would not satisfy the requirement of a quantitative assay that must be simple and easy to perform outside of a lab environment.

Another commonly used method of detecting a dual antibody binding event is Förster/fluorescence resonance energy transfer ("FRET") technology. In typical FRET assays, different chromophores are attached to each antibody. When these antibodies come in close proximity to each other, energy is transferred from one chromophore to the other chromophore. The output of FRET can either be a gain of a fluorescence signal (if two appropriate chromophores are utilized) or a loss in fluorescence signal (if a chromophore and a "quencher" are utilized). Unfortunately, antibody based FRET technology would not be useful in a system for detecting SEB since the signal produced from FRET is typically weak and requires either a high degree of amplification or a situation where many FRET based interaction are occurring in order to be measurable and quantitative. Additionally, the use of antibodies would require multiple incubation and wash steps (3-4 hours) as non-specific FRET interactions may occur if the two antibodies come in close contact within the solution. Consequently, a simple FRET based assay would not work for a quantitative assay that must be simple and easy to perform outside of a lab environment.

Accordingly, in one aspect, a method for detection of a target in a sample, the method comprising the steps of: providing an assay mixture comprising: (i) a first probe comprising a first antibody recognizing a first epitope of the target, the first antibody conjugated to an RNA oligonucleotide; (ii) a second probe comprising a second antibody recognizing a second epitope of the target, the second antibody conjugated to a DNA oligonucleotide; (iii) a reverse primer, wherein the reverse primer comprises a first region complimentary to the RNA oligonucleotide, and a second region complimentary to the DNA oligonucleotide; and (iv) a reverse transcriptase, wherein the reverse transcriptase creates a DNA transcription product from the RNA oligonucleotide using the reverse primer only if the RNA oligonucleotide and the DNA oligonucleotide are in close proximity; adding the sample to the assay mixture to create a reaction mixture; incubating the reaction mixture for a predetermined period of time under conditions suitable for reverse transcription by the reverse transcriptase; and analyzing the reaction mixture for the presence of the DNA transcription product of the RNA oligonucleotide; wherein when the target is present in the sample, and the first antibody is interacting with the first epitope, and the second antibody is interacting with the second epitope, the first region of the reverse primer binds the RNA oligonucleotide and the second region of the reverse primer binds the DNA oligonucleotide to bring the RNA oligonucleotide and the DNA oligonucleotide in close proximity; and wherein the presence of the DNA transcription product indicates the presence of the target in the sample.

In some embodiments, the first antibody is conjugated to the 5' end of the RNA oligonucleotide.

In some embodiments, the second antibody is conjugated to the 3' end of the DNA oligonucleotide.

In some embodiments, the first region of the reverse primer is complimentary to the 3' end of the RNA oligonucleotide.

In some embodiments, the first region of the reverse primer comprises up to approximately eight nucleotides.

In some embodiments, the second region of the reverse primer is complimentary to the 5' end of the DNA oligonucleotide.

In some embodiments, the assay mixture further comprises: (i) a DNA polymerase; (ii) a forward primer complimentary to at least a portion of the DNA transcription product and (iii) a detection probe comprising an oligonucleotide complimentary to at least a portion of the DNA transcription product, and further comprising a fluorophore at one end of the oligonucleotide and a quencher at the opposite end of the oligonucleotide; and further comprising the steps of: inactivating the reverse transcriptase; and incubating the reaction mixture for a predetermined period of time under conditions suitable for qPCR.

In some embodiments, the method includes the step of incubating the sample with an antibody prior to the step of adding the sample to the assay mixture.

In some embodiments, the assay mixture further comprises a modified DNA oligonucleotide complimentary to at least a portion of the RNA oligonucleotide.

In some embodiments, the modification is selected from the group consisting of a 3' spacer, a 3' chain terminator, a 3' fluorochrome, and combinations thereof.

In some embodiments, the assay mixture further comprises a detection probe comprising an oligonucleotide complimentary to at least a portion of the RNA oligonucleotide.

In one aspect, a method for detection of a target in a sample, the method comprising the steps of; providing an assay mixture comprising: (i) a first probe comprising a first antibody recognizing a first epitope of the target, the first antibody conjugated to the 5' end of an RNA oligonucleotide; (ii) a second probe comprising a second antibody recognizing a second epitope of the target, the second antibody conjugated to the 3' end of a DNA oligonucleotide; (iii) a reverse primer, wherein the reverse primer comprises a first region complimentary to 3' end of the RNA oligonucleotide, and a second region complimentary to the 5' end of the DNA oligonucleotide; (iv) a reverse transcriptase, wherein the reverse transcriptase creates a DNA transcription product from the RNA oligonucleotide using the reverse primer only if the RNA oligonucleotide and the DNA oligonucleotide are in close proximity; (v) a DNA polymerase; (vi) a forward primer complimentary to at least a portion of a DNA transcription product; and (vii) a detection probe comprising an oligonucleotide complimentary to at least a portion of the DNA transcription product, and further comprising a fluorophore at one end of the oligonucleotide and a quencher at the opposite end of the oligonucleotide; adding the sample to the assay mixture to create a reaction mixture; incubating the reaction mixture for a predetermined period of time under conditions suitable for reverse transcription by the reverse transcriptase; inactivating the reverse transcriptase; and incubating the reaction mixture for a predetermined period of time under conditions suitable for qPCR; wherein when the target is present in the sample, and the first antibody is interacting with the first epitope, and the second antibody is interacting with the second epitope, the first region of the reverse primer binds the RNA oligonucleotide and the second region of the reverse primer binds the DNA oligonucleotide to bring the RNA oligonucleotide and the DNA oligonucleotide in close proximity.

In some embodiments, the method includes the step of analyzing the reaction mixture for the presence of the DNA transcription product of the RNA oligonucleotide, wherein the presence of the DNA transcription product indicates the presence of the target in the sample.

In some embodiments, the method includes the step of analyzing the reaction mixture for fluorescence from the detection probe, wherein the presence of fluorescence from the detection probe indicates the presence of the target in the sample.

In one aspect, a kit for detection of a target in a sample, including: an as say mixture comprising: (i) a first probe comprising a first antibody recognizing a first epitope of the target, the first antibody conjugated to an RNA oligonucleotide; (ii) a second probe comprising a second antibody recognizing a second epitope of the target, the second antibody conjugated to a DNA oligonucleotide; (iii) a reverse primer, wherein the reverse primer comprises a first region complimentary to the RNA oligonucleotide, and a second region complimentary to the DNA oligonucleotide; and (iv) a reverse transcriptase.

In some embodiments, one or more components of the assay mixture are stored separately from the remainder of the components prior to use of the assay mixture.

In some embodiments, the assay mixture further comprises: (i) a DNA polymerase; (ii) a forward primer complimentary to at least a portion of the DNA transcription product and (iii) a detection probe comprising an oligonucleotide complimentary to at least a portion of the DNA transcription product, and further comprising a fluorophore at one end of the oligonucleotide and a quencher at the opposite end of the oligonucleotide.

In some embodiments, the first antibody is conjugated to the 5' end of the RNA oligonucleotide.

In some embodiments, the second antibody is conjugated to the 3' end of the DNA oligonucleotide.

In some embodiments, the first region of the reverse primer is complimentary to the 3' end of the RNA oligonucleotide.

In some embodiments, the first region of the reverse primer comprises up to approximately eight nucleotides.

In some embodiments, the second region of the reverse primer is complimentary to the 5' end of the DNA oligonucleotide.

In some embodiments, the assay mixture further comprises a modified DNA oligonucleotide complimentary to at least a portion of the RNA oligonucleotide. In some embodiments, the modification is selected from the group consisting of a 3' spacer, a 3' chain terminator, a 3' fluorochrome, and combinations thereof.

In some embodiments, the assay mixture further comprises a detection probe comprising an oligonucleotide complimentary to at least a portion of the RNA oligonucleotide.

BRIEF DESCRIPTION OF THE DRAWINGS

The present invention will be more fully understood and appreciated by reading the following Detailed Description in conjunction with the accompanying drawings, in which.

DETAILED DESCRIPTION

In contrast to ELISA and FRET, PAPA—a new type of Oligonucleotide Linked Immunosorbent Assay ("OLISA")—is capable of detecting a dual antibody binding event by producing a strong signal while avoiding multiple wash and incubation steps. See, for example, FIGS. 1 through 6.

Figure 1:
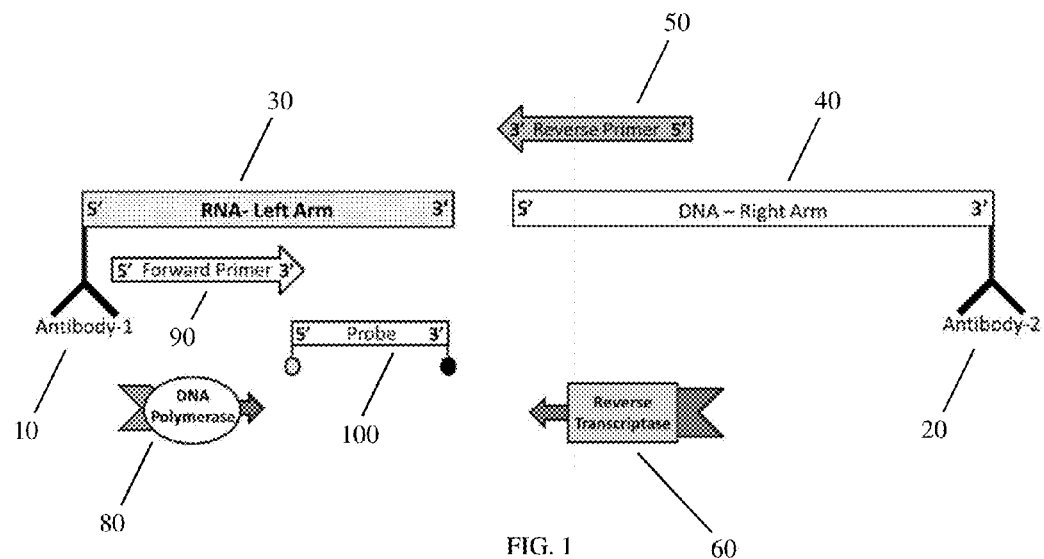
FIG. 1 is a diagrammatic representation of the assay components of the fluorescence-based assay in accordance with an embodiment.

According to an embodiment, the assay consists of two distinct antibody clones (Antibody-1 denoted by numeral 10 and Antibody-2 denoted by numeral 20) that recognize two different epitopes on the same molecule (See FIG. 1). Each of the antibody clones are conjugated or "linked" to oligonucleotides of a specified sequence and type. Antibody-1 is conjugated to an RNA oligonucleotide at its 5' end, referred to as the RNA-left arm 30. Antibody-2 is conjugated to a DNA oligonucleotide at its 3' end, referred to as the DNA-right arm 40. Also included in the assay mix is a DNA reverse primer 50 that is complimentary to the 5' end of the DNA right arm, with the exception of the 3' end of the DNA reverse primer that possesses a 1 to 8 (the number is dependent on the assay conditions) complimentary nucleotide bases to the 3' end of the RNA-left arm (See FIGS. 1-3).

According to one embodiment, the number of overlapping complimentary bases at the 3' end of the DNA reverse primer which joins the RNA-left arm to the DNA-right arm is a critical element of the assay. Since so few nucleotide bases are involved in this interaction, the energy required to break this bond between the RNA-left arm to the DNA-right arm held together by the DNA reverse primer is minimal, and therefore would not normally occur in solution/suspension. However, when the RNA-left arm and DNA-right arm are brought into close proximity to each other, such as when bound together on the same molecule (See FIG. 2), the interaction becomes much more favorable. Therefore, when held in close proximity, the RNA-left arm and DNA-right arm can be held together with the DNA reverse primer (See FIG. 3).

According to an embodiment, a reverse transcriptase 60 such as M-MLV, or a hot-start reverse transcriptase, among others, is used for the detection of the dual antibody binding event (See FIG. 1). This reverse transcriptase uses the DNA reverse primer and the RNA-left arm to create a DNA single stranded complimentary copy 70 of the RNA-left arm sequence (See FIG. 4). This DNA copy is only created when the RNA-left arm and DNA-right arm are joined together by the DNA reverse primer (with a minimized overlap to the RNA-left arm which cannot initiate the reaction in solutions lacking the target molecule), and thus the DNA copy is only created when Antibody-1 and Antibody-2 are joined together on the same molecule (See FIG. 4). Both the antibody binding and reverse transcriptase steps would occur at or near body temperature (including, but not limited to 37° C. to 42° C.), depending on the assay conditions. According to an embodiment, the reverse transcriptase step will only be allowed to occur for one cycle, and therefore the number of reverse-transcribed DNA copies made will be dependent on the number of molecules present onto which both Antibody-1 and Antibody-2 can bind. This makes the PAPA a quantitative assay.

According to an embodiment, other components are utilized in the assay mix in order to quantify the number of reverse-transcribed DNA copies via a quantitative fluorescence PCR method. For example, these components could include a DNA polymerase 80 with 5' exo-nuclease activity, a DNA forward primer 90 complimentary to the 3' end of the reverse-transcribed DNA, and a DNA probe 100 with a fluorophore and a quencher at opposite ends that is complimentary to the reverse-transcribed DNA (See FIG. 1). To perform quantitative PCR, the temperature is initially raised to 95° C. At this temperature, the DNA polymerase 80, such as a Hot-start DNA polymerase, is activated and non-heat stable proteins, such as the Reverse Transcriptase 60 and Antibody-1 and Antibody-2 are inactivated. Due to the inactivation of the reverse transcriptase and antibodies, no new reverse-transcribed DNA copies can be made. After this step, normal qPCR protocols can be followed. Temperatures are sequentially changed from the annealing (50-65° C.), to the elongation (55-72° C.), to the denaturation (95° C.) phases for each PCR cycle. During every cycle, a fluorescent signal is generated due to the separation of the fluorophore and quencher on a probe that is bound to a DNA template being transcribed by the DNA polymerase with 5'exonuclease activity (See FIGS. 5-6). The fluorescence signals increase throughout the PCR cycles until the signal exceeds a threshold, called the threshold cycle ("Ct"). The threshold cycle, or the cycle at which the fluorescence threshold is reached, is relative to the amount of starting material/Reverse-transcribed DNA copies/target molecules. Therefore, the PAPA is as quantifiable as a qPCR assay. In addition to the Ct value, the maximum fluorescence output of the assay can be used to quantify the amount of starting material/reverse-transcribed DNA copies/target molecules in the assay.

According to an embodiment, other components can be added to the assay to reduce background signals within the PAPA. One such set of components, for example, would prevent the non-specific binding of DNA oligonucleotides to the RNA oligonucleotides. This can be accomplished by utilizing modified DNA oligonucleotides that possess a complimentary sequence to that of the RNA oligonucleotide. The modification on the DNA oligonucleotide would prevent the DNA nucleotide from being extended (i.e. used as a primer) by the DNA or RNA polymerase (reverse transcriptase). This modified DNA oligonucleotide is referred to as a "CAP". The CAP can be of any length, as long as it maintains the ability to bind to the RNA oligonucleotide. Examples of modifications that prevent the CAP from being utilized as a primer include but are not limited to 3' spacers (such as C3 spacer), 3' chain terminators (such as dideoxycytidine or dideoxyguanine), and 3' fluorochromes (such as fluorescein). In addition to CAPs, a qPCR probe can also be used to prevent the non-specific binding of DNA oligonucleotides to the RNA oligonucleotide if this probe was designed to be complimentary to a section. This type of blocking qPCR probe is referred to as a "COMP Probe".

According to an embodiment, in order to design a PAPA specific for the detection of unique molecules a few details should be considered. If possible, it should be determined where the two different antibodies bind to on the specified molecule. It is important to determine the orientation of one antibody to the other in order to correctly establish the antibody that should be conjugated with the RNA-left arm vs. the DNA-right arm. If not, a series of experiments may be performed to establish the correct orientation. Another consideration is the distance between the antibody binding sites on the specified molecule. Distance is a factor in that the RNA-left arm needs to be close enough to the DNA-right arm to allow for an overlap to occur. This distance can be compensated for by varying the length of the DNA-right arm (at its 3'end) as long as the complementary sequence for the DNA reverse primer is not affected. Another important factor to consider is minimizing the possibility of "heterodimer" interactions from the various sequences with the Left-RNA template. These interactions have the potential to cause "false-positive" signals (i.e. a positive signal in the absence of a dual-antibody binding event) if the RNA template is primed with a heterodimer sequence (a nucleotide sequence that is not associated with the 3-prime end of the reverse primer) that binds near the 3-prime end of the RNA template. The strength of these non-ideal interactions will be affected by the assay conditions and can be determined through experimental testing.

According to yet another embodiment, there may be an initial antibody block step, such as with an isotype antibody, prior to the addition of the PAPA reagents. An additional wash step may or may not be included.

According to an embodiment, all the components for the PAPA can be added at once without the need for buffer changes, washes, or incubation steps, which sets it apart from many other assays. Similar OLISA technologies, such as the Proximity Ligation Assay ("PLA") and the exonuclease enabled Proximity Extension Assay ("PEA") require multiple wash and incubation steps to produce the positive signals in their laboratory tests. Due to their time consuming and difficult set-up, these technologies are not suited for fieldable applications. Additionally, since fluorochromes are used for the detection signal, the PAPA has the potential to be multiplexed, where more than one molecule or protein can be detected per assay.

Accordingly, the PAPA is a simple and easy to use one-step technology that can be designed to detect and quantify the presence of any molecule in a sample following analysis on any fluorescent PCR-based platform. According to one embodiment, in assays for SEB the SEB-PAPA is designed to detect and identify the toxic potential of SEB molecules found in unknown samples.

Example 1

A methodological procedure for developing and testing a PAPA test using kanamycin resistance gene sequence. Although the kanamycin resistance gene sequence is utilized for the primers, templates, and probes in this version of the PAPA, use of this sequence is not mandatory. Other sequences, and other selective mechanisms, are possible.

As an initial step, the development of the PAPA requires determination of the number of overlapping nucleotides between the reverse primer and RNA-Left Arm required to produce a positive signal in solution (i.e., without the requirement of being in close proximity caused by binding of the associated antibody to the target). This can be accomplished, for example, utilizing an assay comprising the reagents listed or described in FIG. 1. According to one variation, the RNA-Left Arm and DNA-Right Arm will not be linked to or associated with an antibody. According to another variation, the RNA-Left Arm and DNA-Right Arm are linked to or associated with an antibody (including but not limited to the antibody that each element will be linked to in the final, field-deployed assay), but no target is introduced. Without target, the antibodies should not themselves cause the RNA-Left Arm and DNA-Right Arm elements to come into close proximity. According to an embodiment, nucleotide overlaps of 0, 1, 2, 3, 4, 5, 6, 7, and 8 can be utilized to promote the interaction between the RNA-Left Arm and the DNA-Right Arm. See, for example, the sequences listed in TABLE 1. Depending on the assay conditions (i.e. reaction temperature, annealing/elongation times, etc) and components (i.e. salts, enzyme concentration, contaminants, etc), the number of nucleotide overlaps required for the assay to produce a signal with and without a dual antibody binding event will vary. According to one embodiment, the assay can initially be tested in the context of simple qPCR and Reverse Transcriptase PCR, using conditions with a full RNA template or a shortened Left-RNA template (requiring a nucleotide overlap to produce a signal).

According to yet another embodiment, the assay can be modified or made more specific by utilizing one or more oligonucleotide sequences with modified bases. For example, the assay can be designed to utilize oligonucleotides containing isoguanine (iso-dG) and 5'-methylisocytosine (iso-dC), which form specific bonds since iso-dG and iso-dC are unique and only form iso-dG/iso-dC or iso-dC/iso-dG bonds. Another example is the use of hybrid RNA/DNA oligonucleotide sequences. Many other examples of modified oligos are possible in order to increase or otherwise alter specificity in the assay.

Figure 2:
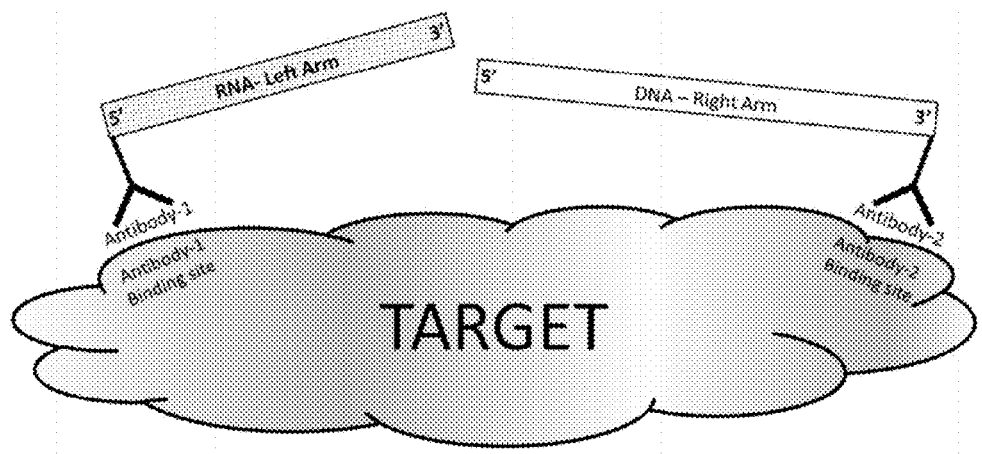
FIG. 2 is a diagrammatic representation of antibodies (conjugated with an oligonucleotide) binding to molecular target in accordance with an embodiment.
Figure 3:
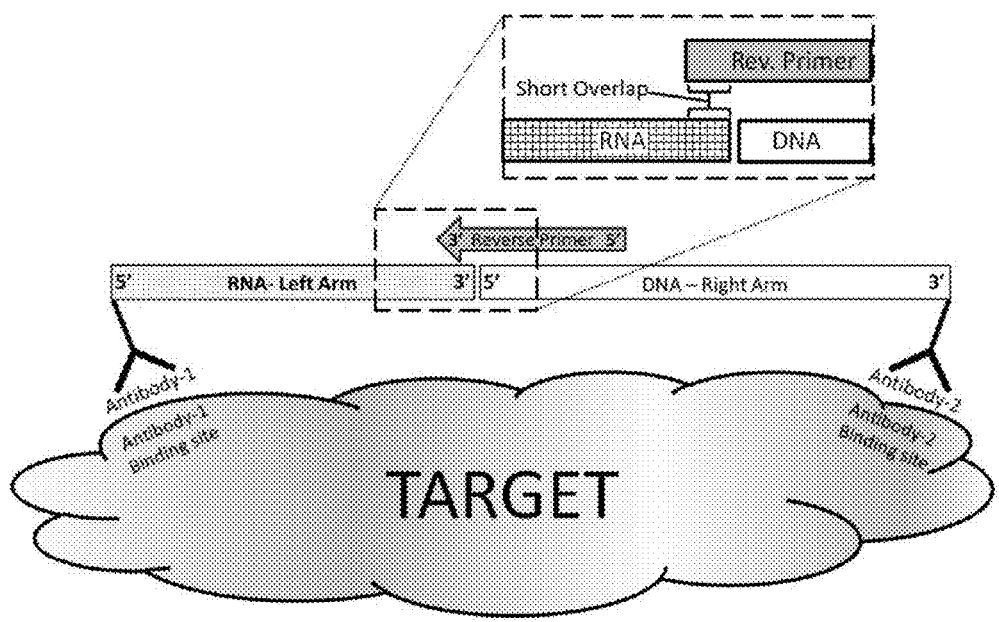
FIG. 3 is a diagrammatic representation of a primer simultaneously binding to a short segment on the RNA-Left Arm element and a short segment on the DNA-Right arm element, which occurs when the two elements are brought together in close proximity after antibodies bind to molecular target, in accordance with an embodiment.
Figure 4:
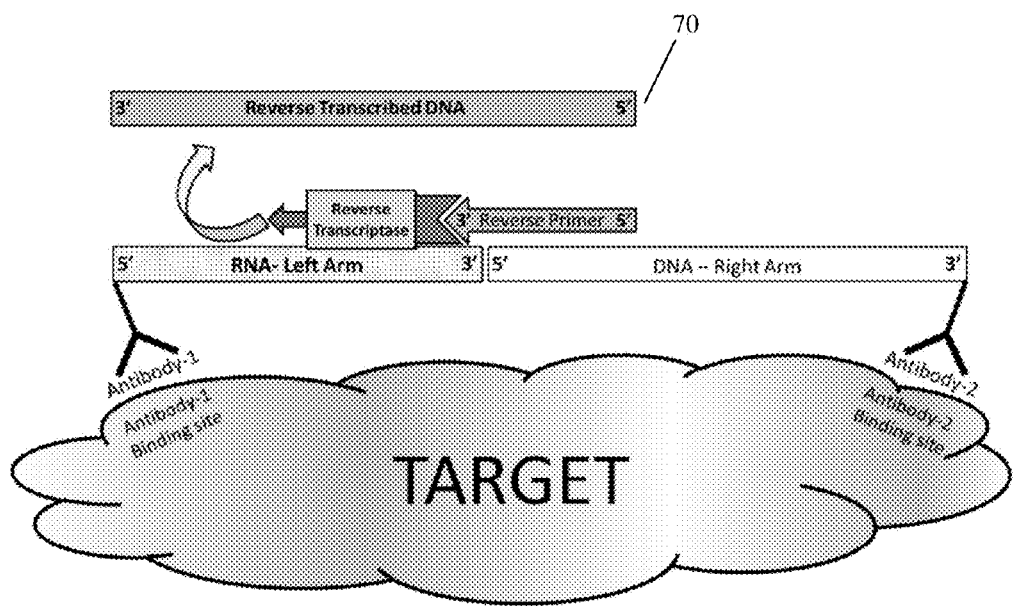
FIG. 4 is a diagrammatic representation of reverse transcriptase synthesizing a single stranded DNA molecule from the RNA-Left Arm template, according to an embodiment.
Figure 5:
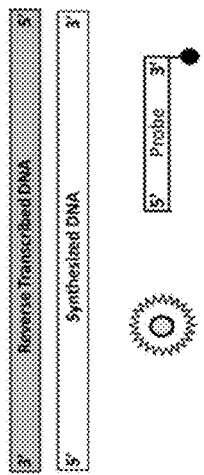
FIG. 5 is a diagrammatic representation of a first cycle of qPCR reaction, in which DNA polymerase synthesizes DNA from the reverse-transcribed DNA template and excises fluorophore from a probe, in accordance with an embodiment.
Figure 5:
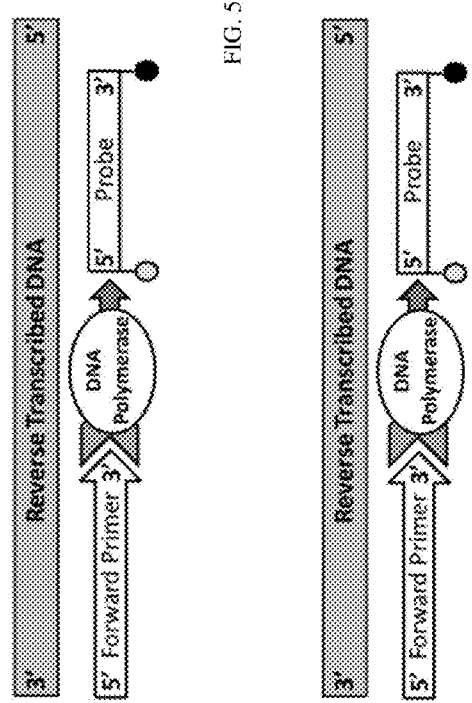
Figure 6:
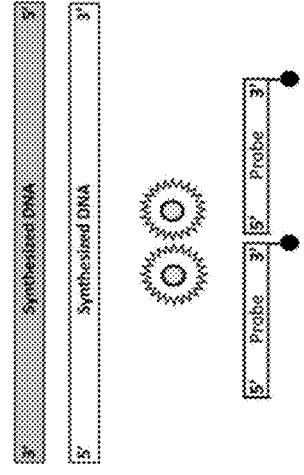
FIG. 6 is a diagrammatic representation of a second cycle of qPCR reaction, in accordance with an embodiment.
Figure 6:
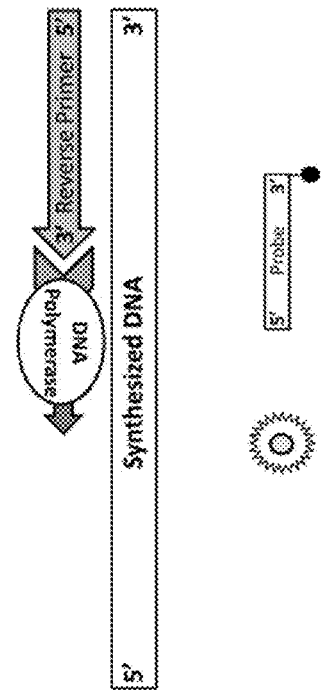
Figure 7:
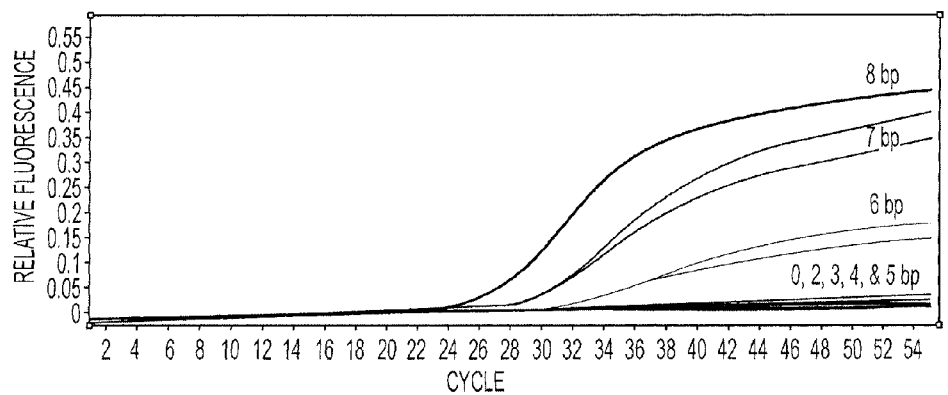
FIG. 7 is a graph of a qPCR reaction in accordance with an embodiment including variations of the Reverse Primers (with differing degrees of nucleotide overlap, from 0 to 8 bp, with the RNA-Left Arm) and preparations of the Left and Right Arms not conjugated to antibodies.

To determine the minimal degree of overlap required to produce a positive signal in a Reverse Transcriptase driven PCR reaction, an assay was set up using preparations of the Left-RNA Arm and Right-DNA Arm in which the "arms" were not conjugated to detection antibodies (FIG. 2). The assay consisted of Forward Primer 2 (500 nM), Probe 2 (100 nM), RNA-Left Arm (not conjugated to an antibody; 1.2× $10^7$ molecules per reaction), DNA-Right Arm 5 (not conjugated to an antibody; 500 nM), Hot-start DNA polymerase (0.025 units per uL), Reverse Transcriptase (M-MLV; 1 unit per uL), DNA polymerase/Reverse Transcriptase buffer mix, and different versions of the Reverse Primers (with differing degrees of nucleotide overlap, from 0 to 8 bp, with the RNA-Left Arm; 500 nM). The reaction was performed with a 5 minute initial Reverse Transcriptase step at 37° C., followed by 94° C. hot start/denaturing step (4 minutes), and then 55 cycles of 94° C. (15 seconds) to 55° C. (30 seconds) in the Rotor-Gene Q qPCR instrument. Based on the results, when Reverse Primers with 6, 7 or 8 bp overlapping nucleotides are used, positive signals are generated in solution in the absence of antibody binding events (FIG. 7). Additionally, no signals are generated when Reverse Primers with 0, 2, 3, 4 or 5 bp overlapping nucleotides are used (FIG. 7). Therefore, antibody binding events would be required in these conditions to generate a signal when Reverse Primers with 2, 3, 4 or 5 bp overlapping nucleotides are used.

TABLE 1

Oligonucleotides utilized for PAPA testing according to an embodiment.

| Oligonucleotide Name | Oligonucleotide Sequence (5' to 3') |
|---|---|
| Kan For 1 | CGAGTGATTTTGATGACGAGCGT (SEQ ID NO: 1) |
| Kan For 2 | AGTGATTTTGATGACGAGCGTAA (SEQ ID NO: 2) |
| Kan For 3 | CGAGTGATTTTGATGACGA (SEQ ID NO: 3) |
| Kan Right 1 DNA Temp | ACCGGATTCAGTCGTCACTCATGGTGATTTC (SEQ ID NO: 4) |
| Kan Right 2 DNA Temp | ACCGGATTCAGTCGTCACTCATGGTGA (SEQ ID NO: 5) |
| Kan Right 3 DNA Temp | ACCGGATTCAGTCGTCACTCATGGT (SEQ ID NO: 6) |
| Kan Right 4 DNA Temp | ACCGGATTCAGTCGTCACTCATGGTGGT (SEQ ID NO: 7) |
| Kan Right 5 DNA Temp | ACCGGATTCAGTCGTCACTCATAATTAA (SEQ ID NO: 8) |
| Kan Right 6 DNA Temp | ACCGGATTCAGTCGTCACTCATCCATAA (SEQ ID NO: 9) |
| Kan Right 7 DNA Temp | ACCGGATTCAGTCGTCACTCATATATAA (SEQ ID NO: 10) |
| Kan Rev 1-8 overlap | CGACTGAATCCGGTGAGAATGG (SEQ ID NO: 11) |
| Kan Rev 1-7 overlap | ACGACTGAATCCGGTGAGAATG (SEQ ID NO: 12) |
| Kan Rev 1-6 overlap | GACGACTGAATCCGGTGAGAAT (SEQ ID NO: 13) |
| Kan Rev 1-5 overlap | TGACGACTGAATCCGGTGAGAA (SEQ ID NO: 14) |
| Kan Rev 1-4 overlap | GTGACGACTGAATCCGGTGAGA (SEQ ID NO: 15) |
| Kan Rev 1-3 overlap | AGTGACGACTGAATCCGGTGAG (SEQ ID NO: 16) |
| Kan Rev 1-2 overlap | GAGTGACGACTGAATCCGGTGA (SEQ ID NO: 17) |
| Kan Rev 1-1 overlap | TGAGTGACGACTGAATCCGGTG (SEQ ID NO: 18) |
| Kan Rev 1-0 overlap | ATGAGTGACGACTGAATCCGGT (SEQ ID NO: 19) |
| Kan Probe 1 | TGGCTGGCCTGTTGAACAAGTCTGGAAAGA (SEQ ID NO: 20) |
| Kan Probe 2 | CTGGCCTGTTGAACAAGTCTGGAAAGAAATG (SEQ ID NO: 21) |
| Kan Probe 3 | AATGGCTGGCCTGTTGAACAAGTCTGGA (SEQ ID NO: 22) |
| Kan COMP Probe 1 | TGGCTGGCCTGTTGAACAAGTCTGGAAAGA (SEQ ID NO: 23) |
| Kan COMP Probe 2 | CATTTCTTTCCAGACTTGTTCAACAGGCCAG (SEQ ID NO: 24 |
| Kan COMP Probe 3 | AATGGCTGGCCTGTTGAACAAGTCTGGA (SEQ ID NO: 25) |

TABLE 1-continued

Oligonucleotides utilized for PAPA testing
according to an embodiment.

| Oligonucleotide Name | Oligonucleotide Sequence (5' to 3') |
|---|---|
| CAP 24 | GAGAATGGCAAAAGCTTATGCATT (SEQ ID NO: 26) |
| CAP 20 | GAGAATGGCAAAAGCTTATG (SEQ ID NO: 27) |
| CAP 28 | GAGAATGGCAAAAGCTTATGCATTTCTT (SEQ ID NO: 28) |
| Kan Full RNA Temp | CGAGUGAUUUUGAUGACGAGCGUAAUGGCUG GCCUGUUGAACAAGUCUGGAAAGAAAUGCAU AAGCUUUUGCCAUUCUCACCGGAUUCAGUCG UCACUCAU (SEQ ID NO: 29) |
| Kan Left RNA Temp | CGAGUGAUUUUGAUGACGAGCGUAAUGGCUG GCCUGUUGAACAAGUCUGGAAAGAAAUGCAU AAGCUUUUGCCAUUCUC (SEQ ID NO: 30) |

As a second step in PAPA testing, antibody binding studies utilizing antibodies conjugated to oligonucleotides can be performed to determine if close proximity can promote PCR. The experiment described above for the first step can be repeated, this time with the RNA-Left Arm and DNA-Right Arm elements conjugated to antibodies (preferably the antibodies that each element will be linked to in the final, field-deployed assay) and target will be introduced to the system. According to an embodiment (see Example 2), antibodies against human insulin from Mercodia (Mab 1 Anti-Insulin and Mab 2 Anti-Insulin) can be utilized, with human insulin (from Tocris) used as the target protein. These Mercodia anti-insulin antibodies have been reported to be successful in an antibody-based proximity ligation assay.

According to another embodiment (see Example 3), antibodies against mouse interleukin-2 (IL-2) from eBioscience (JES6-1A12 and JES6-5H4) can be utilized, with recombinant mouse IL-2 (from eBioscience) as the target protein in the PAPA. These eBioscience anti-insulin antibodies have been utilized in mouse IL-2 ELISA assays.

According to another embodiment (see Example 4), antibodies against SEB (2B33 and B87, both available from Santa Cruz Biotechnology) can be utilized with SEB toxin (from BEI resources) as the target protein in the PAPA. These antibodies target the SEB active (TCR and MHC class II) binding sites. The 2B33 antibody blocks MHC class II binding and the B87 antibody blocks TCR binding.

According to yet another embodiment, any antibody, aptamer or substance/protein/molecule that can specifically (or non-specifically) bind to a target protein or molecule and be conjugated to an oligonucleotide can be utilized in the PAPA.

According to an embodiment, initial studies use a RNA-Left Arm. Additionally, InnovaBiosciences will be utilized initially to conjugate the oligonucleotides to the antibodies. According to an embodiment, the antibodies and target are different from those described herein, and are instead another known or to-be-discovered antibody/antigen recognition pair.

Example 2

Figure 8:
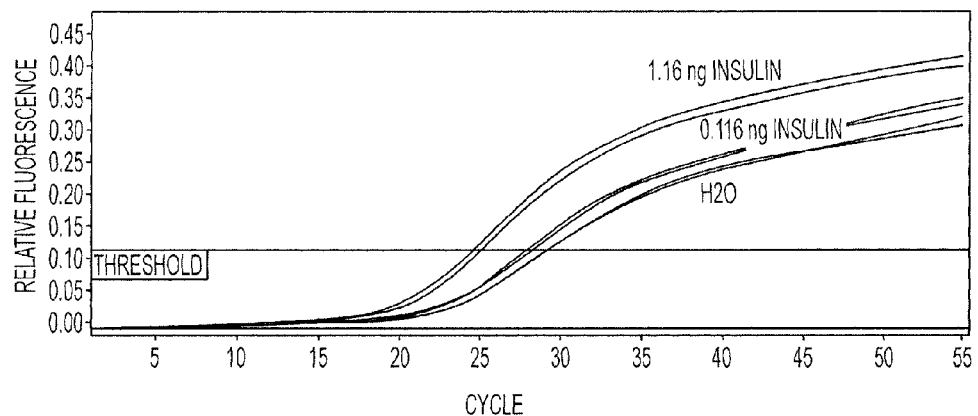
FIG. 8 is a graph of a qPCR reaction analyzing the use of PAPA to detect insulin in accordance with an embodiment.

Experiment to test whether the PAPA can be utilized to detect insulin. Antibodies against human insulin (Mab 1 Anti-Insulin and Mab 2 Anti-Insulin) were obtained from Mercodia and conjugated to RNA (Kan Left RNA Temp) and DNA (Kan Right 5 DNA Temp) oligonucleotides by InnovaBiosciences. These sequences were chosen based on data from supporting experiments. Initial conjugations utilized a 2:1 oligo:antibody ratio. Mab 1 Anti-Insulin antibody was conjugated to the RNA oligo, making it the Anti-Insulin Left-RNA Arm. Mab 2 Anti-Insulin antibody was conjugated to the DNA oligo, making it the Anti-Insulin Right-DNA Arm. The assay consisted of Kan Forward Primer 2 (500 nM), Kan Probe 2 (100 nM), Anti-Insulin Left-RNA Arm ($1.6 \times 10^{10}$ molecules per reaction), Anti-Insulin Right-DNA Arm ($1.6 \times 10^{10}$ molecules per reaction), Hot-start DNA polymerase (0.025 units per uL), Reverse Transcriptase (M-MLV; 1 unit per uL), RNasin (0.4 units per uL), DNA polymerase/Reverse Transcriptase buffer mix, Kan Reverse Primers 1-3 (500 nM) and varying amounts of Insulin (0.116 or 1.16 ng) or H20 (control). The reaction was performed with a 1 hour initial Reverse Transcriptase step at 37° C., followed by 94° C. hot start/denaturing step (4 minutes), and then 55 cycles of 94° C. (15 seconds) to 55° C. (30 seconds) in the Rotor-Gene Q qPCR instrument in a total volume of 15 uL per reaction. The results are shown in FIG. 8. The Insulin PAPA is able to detect both concentrations of Insulin (0.116 and 1.16 ng) compared to the H20 samples, with lower Ct values and higher fluorescent outputs for the Insulin samples compared to the H20 samples. In addition, the highest concentrations of Insulin (1.16 ng) produced the lowest Ct values and highest fluorescent outputs, indicating that the assay results correlate to the amount of target added.

Example 3

Figure 9:
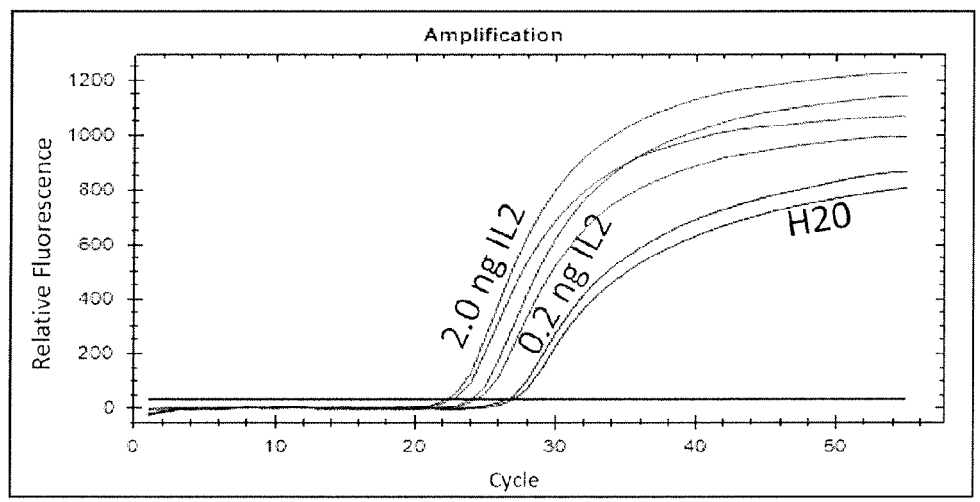
FIG. 9 is a graph of a qPCR reaction analyzing the use of PAPA to detect IL-2 in accordance with an embodiment.

Experiment to test whether the PAPA can be utilized to detect IL-2. Antibodies against mouse IL-2 (JES6-1A12 and JES6-5H4) were obtained from eBioscience and conjugated to RNA (Kan Left RNA Temp) and DNA (Kan Right 5 DNA Temp) oligonucleotides by InnovaBiosciences. These sequences were chosen based on data from supporting experiments. Initial conjugations utilized a 2:1 oligo:antibody ratio. The JES6-1A12 Anti-IL-2 antibody was conjugated to the RNA oligo, making it the Anti-IL-2 Left-RNA Arm. The JES6-5H4 Anti-IL-2 antibody was conjugated to the DNA olgio, making it the Anti-IL-2 Right-DNA Arm. The assay consisted of Kan Forward Primer 2 (500 nM), Kan Probe 2 (100 nM), Anti-IL-2 Left-RNA Arm ($1.6 \times 10^{10}$ molecules), Anti-IL-2 Right-DNA Arm ($1.6 \times 10^{10}$ molecules per reaction), Hot-start DNA polymerase (0.025 units per uL), Reverse Transcriptase (M-MLV; 1 unit per uL), RNasin (0.4 units per uL), DNA polymerase/Reverse Transcriptase buffer mix, Kan Reverse Primers 1-3 (500 nM) and varying amounts of IL-2 (0.20 or 2.0 ng) or H20 (control). The reaction was performed with a 1 hour initial Reverse Transcriptase step at 37° C., followed by 94° C. hot start/denaturing step (4 minutes), and then 55 cycles of 94° C. (15 seconds) to 55° C. (30 seconds) in the Rotor-Gene Q qPCR instrument in a total volume of 15 uL per reaction. The results are shown in FIG. 9. The IL-2 PAPA is able to detect both concentrations of IL-2 (0.20 and 2.0 ng) compared to the H20 samples, with lower Ct values and higher fluorescent outputs for the IL-2 samples compared to the H20 samples. In addition, the highest concentrations of IL-2 (2.0 ng) produced the lowest Ct values and highest fluorescent outputs, indicating that the assay results correlate to the amount of target added.

Example 4

Figure 10A:
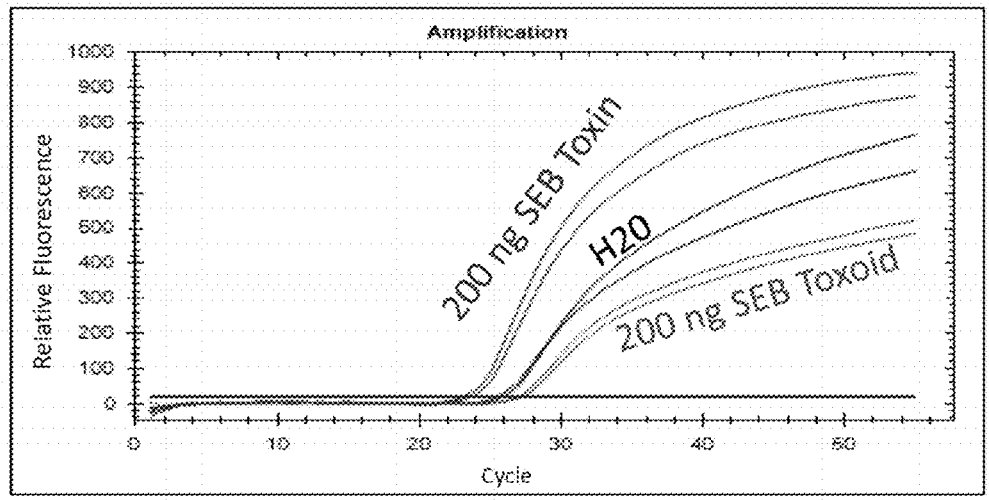
FIG. 10A is a graph of a qPCR reaction analyzing the use of PAPA to detect active SEB toxin compared to inactive SEB toxoid in accordance with an embodiment.
Figure 10B:
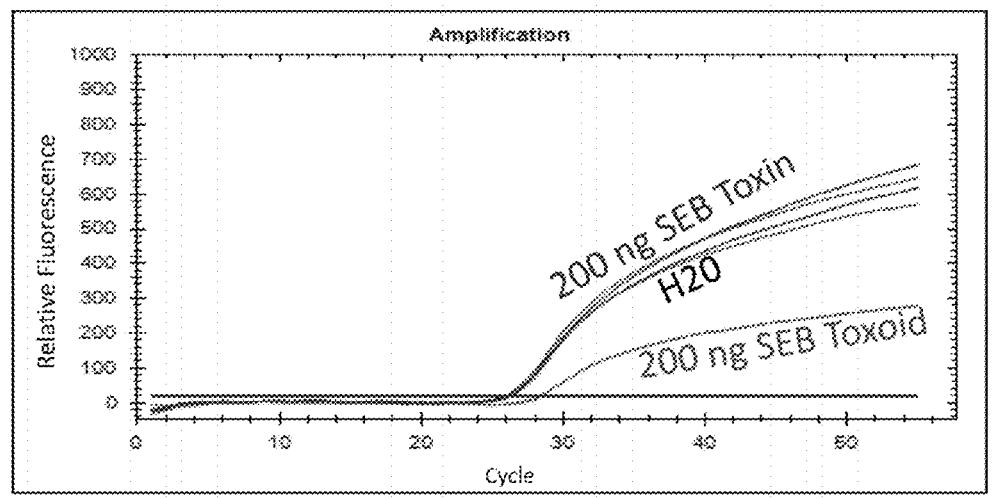
FIG. 10B is a graph of a qPCR reaction analyzing the use of PAPA and control isotype antibodies to detect active SEB toxin or inactive SEB toxoid in accordance with an embodiment.

Experiment to test whether the PAPA can be utilized to detect active SEB toxin versus inactive SEB toxoid. Antibodies against SEB (2B33 and B87) or an isotype control (eBioscience, Rat IgG2a) were conjugated to RNA (Kan Left RNA Temp) and DNA (Kan Right DNA Temp) oligonucleotides by InnovaBiosciences. These sequences were chosen based on data from supporting experiments. Initial conjugations utilized a 2:1 oligo:antibody ratio. The 2B33 Anti-SEB antibody was conjugated to the RNA oligo, making it the Anti-SEB Left-RNA Arm. The B87 Anti-SEB antibody was conjugated to the DNA olgio, making it the Anti-SEB Right-DNA Arm. For a control, the isotype antibody was also conjugated to the RNA and DNA oligos, making a Control Left-RNA Arm and Control Right-DNA Arm, respectively. The SEB assay consisted of Kan Forward Primer 2 (500 nM), Kan Probe 2 (100 nM), Anti-SEB Left-RNA Arm ($1.6 \times 10^{10}$ molecules per reaction), Anti-SEB Right-DNA Arm ($1.6 \times 10^{10}$ molecules per reaction), Hot-start DNA polymerase (0.025 units per uL), Reverse Transcriptase (M-MLV; 1 unit per uL), RNasin (0.4 units per uL), DNA polymerase/Reverse Transcriptase buffer mix, Kan Reverse Primers 1-3 (500 nM) and added SEB toxin (BEI, 200 ng), inactivated SEB toxoid (BEI, 200 ng) or H20 (control). The control assay consisted of the same components above, with the Control Arms being used in place of the SEB Arms. The reaction was performed with a 5 minute initial Reverse Transcriptase step at 37° C., followed by 94° C. hot start/denaturing step (4 minutes), and then 55 cycles of 94° C. (15 seconds) to 55° C. (30 seconds) in the BioRad CFX96 qPCR instrument in a total volume of 15 uL per reaction. The results are shown in FIG. 10A and FIG. 10B. The SEB PAPA is able to detect the active SEB toxin samples compared to the H20 and inactive SEB toxoid samples, with lower Ct values and higher fluorescent outputs for the SEB toxin compared to the H20 and SEB toxoid samples (FIG. 10A). This indicates that the SEB PAPA is specific for active SEB toxin (FIG. 10A). The Control PAPA shows that there are no differences between SEB toxin samples compared to the H20 samples, with similar Ct values and fluorescent outputs, indicating that the SEB toxin is not detected in the Control PAPA (FIG. 10B). The SEB toxoid produces higher Ct values and lower fluorescent outputs, indicating that the SEB toxoid is also not detected in the Control PAPA (FIG. 10B).

Example 5

Figure 11:
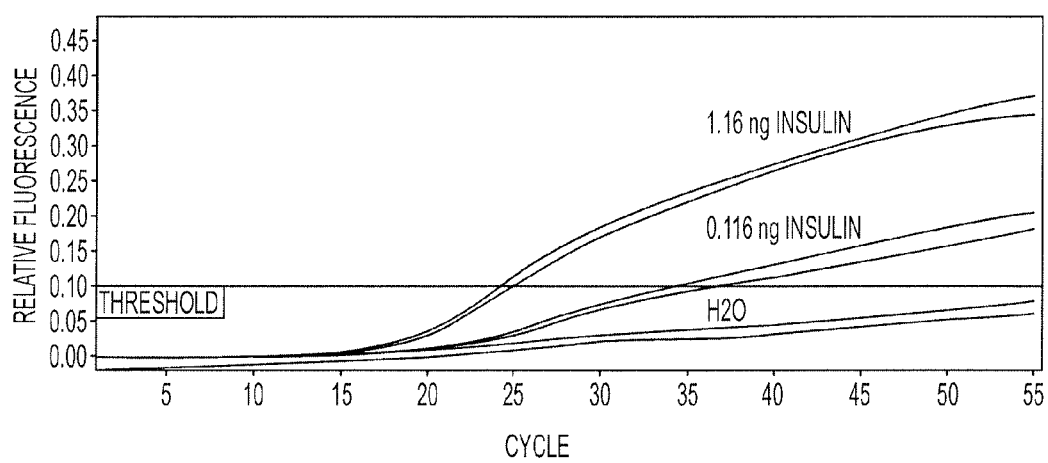
FIG. 11 is a graph of a qPCR reaction analyzing the use of PAPA with CAPs and COMP Probe (to reduce background) to detect insulin in accordance with an embodiment.

Experiment to test whether the PAPA with CAPs and COMP Probe can be utilized to detect insulin. Antibodies against human insulin (Mab 1 Anti-Insulin and Mab 2 Anti-Insulin) were obtained from Mercodia and conjugated to RNA (Kan Left RNA Temp) and DNA (Kan Right 5 DNA Temp) oligonucleotides by InnovaBiosciences. These sequences were chosen based on data from supporting experiments. Initial conjugations utilized a 2:1 oligo:antibody ratio. Mab 1 Anti-Insulin antibody was conjugated to the RNA oligo, making it the Anti-Insulin Left-RNA Arm. Mab 2 Anti-Insulin antibody was conjugated to the DNA olgio, making it the Anti-Insulin Right-DNA Arm. The assay consisted of Kan Forward Primer 2 (500 nM), Kan COMP Probe 2 (100 nM), CAP 20 (1.3 uM), Anti-Insulin Left-RNA Arm ($1.6 \times 10^{10}$ molecules per reaction), Anti-Insulin Right-DNA Arm ($1.6 \times 10^{10}$ molecules per reaction), Hot-start DNA polymerase (0.025 units per uL), Reverse Transcriptase (M-MLV; 1 unit per uL), RNasin (0.4 units per uL), DNA polymerase/Reverse Transcriptase buffer mix, Kan Reverse Primers 1-3 (500 nM) and varying amounts of Insulin (0.116 or 1.16 ng) or H20 (control). The reaction was performed with a 1 hour initial Reverse Transcriptase step at 37° C., followed by 94° C. hot start/denaturing step (4 minutes), and then 55 cycles of 94° C. (15 seconds) to 55° C. (30 seconds) in the Rotor-Gene Q qPCR instrument in a total volume of 15 uL per reaction. The results are shown in FIG. 11. The Insulin PAPA with CAPs and COMP Probe 2 is able to detect both concentrations of Insulin (0.116 and 1.16 ng) compared to the H20 samples, with lower Ct values and higher fluorescent outputs for the Insulin samples compared to the H20 samples. In addition, the highest concentrations of Insulin (1.16 ng) produced the lowest Ct values and highest fluorescent outputs, indicating that the assay results correlate to the amount of target added. Compared to the Insulin PAPA without CAPs and COMP Probe 2 (FIG. 8), less background signal is produced when CAPs and COMP Probe 2 are present in the PAPA (FIG. 11).

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method for detection of a target in a sample, the method comprising the steps of;
   providing an assay mixture comprising: (i) a first probe comprising a first antibody recognizing a first epitope of the target, the first antibody conjugated to an RNA oligonucleotide; (ii) a second probe comprising a second antibody recognizing a second epitope of the target, the second antibody conjugated to a DNA oligonucleotide; (iii) a reverse primer, wherein the reverse primer comprises a first region complementary to the RNA oligonucleotide, and a second region complementary to said DNA oligonucleotide; and (iv) a reverse transcriptase, wherein said reverse transcriptase creates a DNA transcription product from the RNA oligonucleotide using said reverse primer only if said RNA oligonucleotide and said DNA oligonucleotide are in close proximity;
   adding the sample to the assay mixture to create a reaction mixture;
   incubating the reaction mixture for a predetermined period of time under conditions suitable for reverse transcription by said reverse transcriptase; and
   analyzing said reaction mixture for the presence of said DNA transcription product of the RNA oligonucleotide;
   wherein when the target is present in the sample, and the first antibody is interacting with the first epitope, and the second antibody is interacting with the second epitope, the first region of the reverse primer binds the RNA oligonucleotide and the second region of the reverse primer binds the DNA oligonucleotide to bring the RNA oligonucleotide and the DNA oligonucleotide in close proximity;
   wherein the presence of said DNA transcription product indicates the presence of the target in said sample.

2. The method of claim 1, wherein the first antibody is conjugated to the 5' end of the RNA oligonucleotide.

3. The method of claim 1, wherein the second antibody is conjugated to the 3' end of the DNA oligonucleotide.

4. The method of claim 1, wherein said first region of the reverse primer is complementary to the 3' end of the RNA oligonucleotide.

5. The method of claim 1, wherein said first region of the reverse primer comprises up to, or approximately, eight nucleotides.

6. The method of claim 1, wherein said second region of the reverse primer is complementary to the 5' end of the DNA oligonucleotide.

7. The method of claim 1, wherein the assay mixture further comprises a modified DNA oligonucleotide, said modified DNA oligonucleotide complementary to at least a portion of said RNA oligonucleotide.

8. The method of claim 7, wherein said modification is selected from the group consisting of a 3' spacer, a 3' chain terminator, a 3' fluorochrome, and combinations thereof.

9. The method of claim 1, wherein the assay mixture further comprises a detection probe comprising an oligonucleotide complementary to at least a portion of said RNA oligonucleotide.

10. The method of claim 1, wherein said assay mixture further comprises: (i) a DNA polymerase; (ii) a forward primer complementary to at least a portion of said DNA transcription product and (iii) a detection probe comprising an oligonucleotide complementary to at least a portion of said DNA transcription product, and further comprising a fluorophore at one end of the oligonucleotide and a quencher at the opposite end of the oligonucleotide; and further comprising the steps of:
inactivating said reverse transcriptase; and
incubating the reaction mixture for a predetermined period of time under conditions suitable for qPCR.

11. The method of claim 1, further comprising the step of incubating said sample with an antibody prior to the step of adding said sample to said assay mixture.

12. A method for detection of a target in a sample, the method comprising the steps of;
providing an assay mixture comprising: (i) a first probe comprising a first antibody recognizing a first epitope of the target, the first antibody conjugated to the 5' end of an RNA oligonucleotide; (ii) a second probe comprising a second antibody recognizing a second epitope of the target, the second antibody conjugated to the 3' end of a DNA oligonucleotide; (iii) a reverse primer, wherein the reverse primer comprises a first region complementary to 3' end of the RNA oligonucleotide, and a second region complementary to the 5' end of said DNA oligonucleotide; (iv) a reverse transcriptase, wherein said reverse transcriptase creates a DNA transcription product from the RNA oligonucleotide using said reverse primer only if said RNA oligonucleotide and said DNA oligonucleotide are in close proximity; (v) a DNA polymerase; (vi) a forward primer complementary to at least a portion of a DNA transcription product; and (vii) a detection probe comprising an oligonucleotide complementary to at least a portion of said DNA transcription product, and further comprising a fluorophore at one end of the oligonucleotide and a quencher at the opposite end of the oligonucleotide;
adding the sample to the assay mixture to create a reaction mixture;
incubating the reaction mixture for a predetermined period of time under conditions suitable for reverse transcription by said reverse transcriptase;
inactivating said reverse transcriptase; and
incubating the reaction mixture for a predetermined period of time under conditions suitable for qPCR;
wherein when the target is present in the sample, and the first antibody is interacting with the first epitope, and the second antibody is interacting with the second epitope, the first region of the reverse primer binds the RNA oligonucleotide and the second region of the reverse primer binds the DNA oligonucleotide to bring the RNA oligonucleotide and the DNA oligonucleotide in close proximity.

13. The method of claim 12, further comprising the step of analyzing said reaction mixture for the presence of said DNA transcription product of the RNA oligonucleotide, wherein the presence of said DNA transcription product indicates the presence of the target in said sample.

14. The method of claim 12, further comprising the step of analyzing said reaction mixture for fluorescence from said detection probe, wherein the presence of fluorescence from said detection probe indicates the presence of the target in said sample.

15. A kit for detection of a target in a sample, the kit comprising:
an assay mixture comprising: (i) a first probe comprising a first antibody recognizing a first epitope of the target, the first antibody conjugated to an RNA oligonucleotide; (ii) a second probe comprising a second antibody recognizing a second epitope of the target, the second antibody conjugated to a DNA oligonucleotide; (iii) a reverse primer, wherein the reverse primer comprises a first region complementary to the RNA oligonucleotide, and a second region complementary to said DNA oligonucleotide; and (iv) a reverse transcriptase.

16. The kit of claim 15, wherein said assay mixture further comprises: (i) a DNA polymerase; (ii) a forward primer complementary to at least a portion of said DNA transcription product and (iii) a detection probe comprising an oligonucleotide complementary to at least a portion of said DNA transcription product, and further comprising a fluorophore at one end of the oligonucleotide and a quencher at the opposite end of the oligonucleotide.

17. The kit of claim 15, wherein the assay mixture further comprises a modified DNA oligonucleotide, said modified DNA oligonucleotide complementary to at least a portion of said RNA oligonucleotide.

18. The kit of claim 17, wherein said modification is selected from the group consisting of a 3' spacer, a 3' chain terminator, a 3' fluorochrome, and combinations thereof.

19. The kit of claim 15, wherein the assay mixture further comprises a detection probe comprising an oligonucleotide complementary to at least a portion of said RNA oligonucleotide.

* * * * *

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence -continued

```
<220> FEATURE:
<223> OTHER INFORMATION: Primer

<400> SEQUENCE: 1
cgagtgattt tgatgacgag cgt                                           23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
agtgattttg atgacgagcg taa                                           23

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
cgagtgattt tgatgacga                                                19

<210> SEQ ID NO 4
<211> LENGTH: 31
<212> TYPE: DNA
<213> ORGANISM: Artificial Sequence
<220> FEATURE:
<223> OTHER INFORMATION: Probe

<400> SEQUENCE: 4
accggattca gtcgtcactc atggtgattt c                                  31

<210> SEQ ID NO 5
<211> LENGTH: 27
<212> TYPE: DNA
<213> ORGANISM: Artificial Sequence
<220> FEATURE:
<223> OTHER INFORMATION: Probe

<400> SEQUENCE: 5
accggattca gtcgtcactc atggtga                                       27

<210> SEQ ID NO 6
<211> LENGTH: 25
<212> TYPE: DNA
<213> ORGANISM: Artificial Sequence
<220> FEATURE:
<223> OTHER INFORMATION: Probe

<400> SEQUENCE: 6
accggattca gtcgtcactc atggt                                         25

<210> SEQ ID NO 7
<211> LENGTH: 28
<212> TYPE: DNA
<213> ORGANISM: Artificial Sequence
<220> FEATURE:
<223> OTHER INFORMATION: Probe

<400> SEQUENCE: 7
accggattca gtcgtcactc atggtggt                                      28
```

<210> SEQ ID NO 8
<211> LENGTH: 28
<212> TYPE: DNA
<213> ORGANISM: Artificial Sequence
<220> FEATURE:
<223> OTHER INFORMATION: Probe

<400> SEQUENCE: 8
accggattca gtcgtcactc ataattaa                                    28

<210> SEQ ID NO 9
<211> LENGTH: 28
<212> TYPE: DNA
<213> ORGANISM: Artificial Sequence
<220> FEATURE:
<223> OTHER INFORMATION: Probe

<400> SEQUENCE: 9
accggattca gtcgtcactc atccataa                                    28

<210> SEQ ID NO 10
<211> LENGTH: 28
<212> TYPE: DNA
<213> ORGANISM: Artificial Sequence
<220> FEATURE:
<223> OTHER INFORMATION: Probe

<400> SEQUENCE: 10
accggattca gtcgtcactc atatataa                                    28

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
cgactgaatc cggtgagaat gg                                          22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
acgactgaat ccggtgagaa tg                                          22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
gacgactgaa tccggtgaga at                                          22

<210> SEQ ID NO 14
<211> LENGTH: 22
<212> TYPE: DNA
<213> ORGANISM: Artificial Sequence
<220> FEATURE:
<223> OTHER INFORMATION: Primer

```
<400> SEQUENCE: 14
tgacgactga atccggtgag aa                                      22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gtgacgactg aatccggtga ga                                      22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
agtgacgact gaatccggtg ag                                      22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gagtgacgac tgaatccggt ga                                      22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
tgagtgacga ctgaatccgg tg                                      22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
atgagtgacg actgaatccg gt                                      22

<210> SEQ ID NO 20
<211> LENGTH: 30
<212> TYPE: DNA
<213> ORGANISM: Artificial Sequence
<220> FEATURE:
<223> OTHER INFORMATION: Probe

<400> SEQUENCE: 20
tggctggcct gttgaacaag tctggaaaga                              30

<210> SEQ ID NO 21
```

```
<211> LENGTH: 31
<212> TYPE: DNA
<213> ORGANISM: Artificial Sequence
<220> FEATURE:
<223> OTHER INFORMATION: Probe

<400> SEQUENCE: 21
ctggcctgtt gaacaagtct ggaaagaaat g                                      31

<210> SEQ ID NO 22
<211> LENGTH: 28
<212> TYPE: DNA
<213> ORGANISM: Artificial Sequence
<220> FEATURE:
<223> OTHER INFORMATION: Probe

<400> SEQUENCE: 22
aatggctggc ctgttgaaca agtctgga                                          28

<210> SEQ ID NO 23
<211> LENGTH: 30
<212> TYPE: DNA
<213> ORGANISM: Artificial Sequence
<220> FEATURE:
<223> OTHER INFORMATION: Probe

<400> SEQUENCE: 23
tggctggcct gttgaacaag tctggaaaga                                        30

<210> SEQ ID NO 24
<211> LENGTH: 31
<212> TYPE: DNA
<213> ORGANISM: Artificial Sequence
<220> FEATURE:
<223> OTHER INFORMATION: Probe

<400> SEQUENCE: 24
catttctttc cagacttgtt caacaggcca g                                      31

<210> SEQ ID NO 25
<211> LENGTH: 28
<212> TYPE: DNA
<213> ORGANISM: Artificial Sequence
<220> FEATURE:
<223> OTHER INFORMATION: Probe

<400> SEQUENCE: 25
aatggctggc ctgttgaaca agtctgga                                          28

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gagaatggca aaagcttatg catt                                              24

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
```

```
gagaatggca aaagcttatg                                                    20

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
gagaatggca aaagcttatg catttctt                                           28

<210> SEQ ID NO 29
<211> LENGTH: 101
<212> TYPE: RNA
<213> ORGANISM: Artificial Sequence
<220> FEATURE:
<223> OTHER INFORMATION: Probe

<400> SEQUENCE: 29
cgagugauuu ugaugacgag cguaauggcu ggccuguuga acaagucugg aaagaaaugc        60
auaagcuuuu gccauucuca ccggauucag ucgucacuca u                            101

<210> SEQ ID NO 30
<211> LENGTH: 79
<212> TYPE: RNA
<213> ORGANISM: Artificial Sequence
<220> FEATURE:
<223> OTHER INFORMATION: Primer

<400> SEQUENCE: 30
cgagugauuu ugaugacgag cguaauggcu ggccuguuga acaagucugg aaagaaaugc        60
auaagcuuuu gccauucuc                                                     79
```